(12) United States Patent
Huang et al.

(10) Patent No.: US 12,011,249 B2
(45) Date of Patent: Jun. 18, 2024

(54) SYSTEMS AND METHODS FOR TOMOGRAPHY IMAGING

(71) Applicant: SHANGHAI UNITED IMAGING HEALTHCARE CO., LTD., Shanghai (CN)

(72) Inventors: Qinhua Huang, Shanghai (CN); Jianqiao Chen, Shanghai (CN); Shiming Hu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/646,301

(22) Filed: Dec. 29, 2021

(65) Prior Publication Data
US 2022/0117494 A1    Apr. 21, 2022

(30) Foreign Application Priority Data

Dec. 29, 2020  (CN) .......................... 202011607379.4
Dec. 29, 2020  (CN) .......................... 202023282836.5

(51) Int. Cl.
*A61B 5/00* (2006.01)
*G01S 7/52* (2006.01)
*G01S 15/89* (2006.01)

(52) U.S. Cl.
CPC .......... *A61B 5/0095* (2013.01); *A61B 5/7292* (2013.01); *G01S 7/52019* (2013.01); *G01S 15/8993* (2013.01)

(58) Field of Classification Search
CPC . A61B 5/0095; A61B 5/7292; G01S 7/52019; G01S 15/8993
See application file for complete search history.

(56) References Cited

U.S. PATENT DOCUMENTS

| 8,155,729  | B1 * | 4/2012 | Hsieh .................... G01T 1/1603 600/425 |
| 10,004,462 | B2 * | 6/2018 | Ernst ....................... G06T 7/292 |
| 10,635,930 | B2 * | 4/2020 | Geiger ................... G06V 20/64 |

(Continued)

FOREIGN PATENT DOCUMENTS

| CN | 103519789 A | 1/2014 |
| CN | 103829961 A | 6/2014 |

(Continued)

OTHER PUBLICATIONS

Zhang Xiang et al., Full Noncontact Laser Ultrasound: First Human Data, Science & Applications, 8: 1-11, 2019.

*Primary Examiner* — Dixomara Vargas
(74) *Attorney, Agent, or Firm* — METIS IP LLC

(57) ABSTRACT

The present disclosure provides systems and methods for tomography imaging. The systems and methods may obtain an ultrasonic signal indicating a movement state of a position of an object (e.g., a position inside the object). The ultrasonic signal may be acquired by at least one laser ultrasonic component of a medical device. The systems and methods may determine, based on the ultrasonic signal, movement information of the position of the object. The systems and methods may obtain, based on the movement information of the position, target image data of the object using an imaging component of the medical device.

20 Claims, 6 Drawing Sheets

(56) References Cited

U.S. PATENT DOCUMENTS

| | | | | |
|---|---|---|---|---|
| 2008/0287728 | A1* | 11/2008 | Mostafavi | A61N 5/1049 |
| | | | | 128/845 |
| 2011/0216957 | A1 | 9/2011 | Hsieh et al. | |
| 2014/0073904 | A1* | 3/2014 | Biber | A61B 6/527 |
| | | | | 600/410 |
| 2014/0210470 | A1* | 7/2014 | Xu | A61B 6/0487 |
| | | | | 600/407 |
| 2015/0265220 | A1* | 9/2015 | Ernst | G06T 5/003 |
| | | | | 600/407 |
| 2015/0366527 | A1* | 12/2015 | Yu | A61B 6/527 |
| | | | | 600/407 |
| 2016/0035108 | A1* | 2/2016 | Yu | A61B 5/721 |
| | | | | 382/131 |
| 2016/0073962 | A1* | 3/2016 | Yu | G01R 33/283 |
| | | | | 600/407 |
| 2016/0154075 | A1* | 6/2016 | Song | G01R 33/3621 |
| | | | | 324/322 |
| 2016/0345839 | A1* | 12/2016 | Sethuraman | A61B 8/48 |
| 2017/0319143 | A1* | 11/2017 | Yu | A61B 5/682 |
| 2018/0120396 | A1* | 5/2018 | Weiss | A61B 18/02 |
| 2019/0129026 | A1* | 5/2019 | Sumi | G01S 15/8915 |
| 2019/0209868 | A1* | 7/2019 | Stahl | A61N 5/1039 |
| 2019/0307334 | A1 | 10/2019 | Wang et al. | |
| 2020/0187887 | A1* | 6/2020 | Alon Cohen | A61B 6/547 |
| 2021/0341556 | A1* | 11/2021 | Mallett | G01R 33/383 |
| 2022/0047218 | A1* | 2/2022 | Neuber | A61B 5/704 |
| 2022/0202376 | A1* | 6/2022 | Kaneko | A61B 5/721 |

FOREIGN PATENT DOCUMENTS

| | | |
|---|---|---|
| CN | 107157448 A | 9/2017 |
| CN | 107692975 A | 2/2018 |
| CN | 107909624 A | 4/2018 |

* cited by examiner

SYSTEMS AND METHODS FOR TOMOGRAPHY IMAGING

CROSS-REFERENCE OF RELATED APPLICATION

This application claims priority of Chinese Patent Application No. 202011607379.4, filed on Dec. 29, 2020, and Chinese Patent Application No. 202023282836.5, filed on Dec. 29, 2020, the contents of each of which are hereby incorporated by reference.

TECHNICAL FIELD

The present disclosure generally relates to the technology of the medical device, and more particularly, relates to systems and methods for tomography imaging.

BACKGROUND

Tomography imaging is widely used in a variety of medical treatments and/or diagnostics. Various imaging devices (e.g., an X-ray device, an ultrasonography device, a computed tomography (CT) device, a positron emission tomography (PET) device, or a magnetic resonance imaging (MRI) device) can be used to obtain tomographic images by performing a scan on an object (e.g., a patient). A motion of the object during the scan, such as a motion of portions of the body (e.g., the head, a leg, etc.) or a motion of an internal organ (e.g., the heart, lung(s)), may cause motion artifacts in a reconstructed image. In this case, a diagnosis and/or treatment of a disease based on the reconstructed image including the motion artifacts may be unreliable due to poor image quality. Therefore, it is desirable to develop systems or methods for tomography imaging, thereby reducing or avoiding motion artifacts in imaging.

SUMMARY

In one aspect of the present disclosure, a system is provided. The system may include at least one storage device including a set of instructions, and at least one processor configured to communicate with the at least one storage device. When executing the set of instructions, the at least one processor may be configured to direct the system to perform the following operations. The operations may include obtaining an ultrasonic signal indicating a movement state of a position of an object. The ultrasonic signal may be acquired by at least one laser ultrasonic component of a medical device. The operations may also include determining, based on the ultrasonic signal, movement information of the position of the object. The operations may further include obtaining, based on the movement information of the position, target image data of the object using an imaging component of the medical device.

In some embodiments, the ultrasonic signal may be acquired during a scan of the object using the imaging component or before the scan of the object using the imaging component.

In some embodiments, the imaging component may include at least two detection rings. The at least one laser ultrasonic component may be disposed between the at least two detection rings.

In some embodiments, the imaging component may include a gantry with a bore. The at least one laser ultrasonic component may be disposed at an end of the bore.

In some embodiments, the medical device may include a holder configured to support the at least one laser ultrasonic component.

In some embodiments, each of the at least one laser ultrasonic component may include a first laser source and a second laser source.

In some embodiments, the first laser source may be configured to emit an energy pulse to the object for generating the ultrasonic signal and the second laser source may be configured to detect the ultrasonic signal.

In some embodiments, the obtaining, based on the movement information of the position, target image data of the object using an imaging component of the medical device may include determining, based on the movement information, a parameter set including one or more scan parameters; and obtaining the target image data of the object by causing the imaging component to perform a scan on the object based on the one or more scan parameters.

In some embodiments, the obtaining, based on the movement information of the position, target image data of the object using an imaging component of the medical device may include determining, based on the movement information, a parameter set including one or more image reconstruction parameters; obtaining image data of the object by causing the imaging component to perform a scan on the object; and obtaining the target image data of the object based on the image data of the object and the one or more image reconstruction parameters.

In some embodiments, the obtaining, based on the movement information of the position, target image data of the object using an imaging component of the medical device may include obtaining the target image data of the object by triggering the imaging component to perform a scan according to the movement information.

In some embodiments, the obtaining, based on the movement information of the position, target image data of the object using an imaging component of the medical device may include obtaining initial image data of the object by causing the imaging component to perform a scan on the object; and obtaining the target image data of the object based on the initial image data of the object and the movement information.

In some embodiments, the determining, based on the ultrasonic signal, movement information of the position of the object may include generating, based on the ultrasonic signal, an ultrasonic image or a motion curve of the object; and determining, based on the ultrasonic image or the motion curve of the object, the movement information of the position of the object.

In some embodiments, the ultrasonic signal may indicate the movement state of the position inside the object.

In another aspect of the present disclosure, a system is provided. The system may include a medical device. The medical device may include at least one laser ultrasonic component and an imaging component. The at least one laser ultrasonic component may be configured to acquire an ultrasonic signal indicating a movement state of a position of an object. The imaging component may be configured to acquire, based on the ultrasonic signal, image data of the object.

In some embodiments, the ultrasonic signal may indicate the movement state of the position inside the object.

In some embodiments, the imaging component may include at least two detection rings. The at least one laser ultrasonic component may be disposed between the at least two detection rings.

In some embodiments, the imaging component may include a gantry with a bore. The at least one laser ultrasonic component may be disposed at an end of the bore.

In some embodiments, the imaging device may include a holder configured to support the at least one laser ultrasonic component.

In some embodiments, each of the at least one laser ultrasonic component may include a first laser source and a second laser source.

In some embodiments, the first laser source may be configured to emit an energy pulse to the object for generating the ultrasonic signal and the second laser source may be configured to detect the ultrasonic signal.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Figure 2:
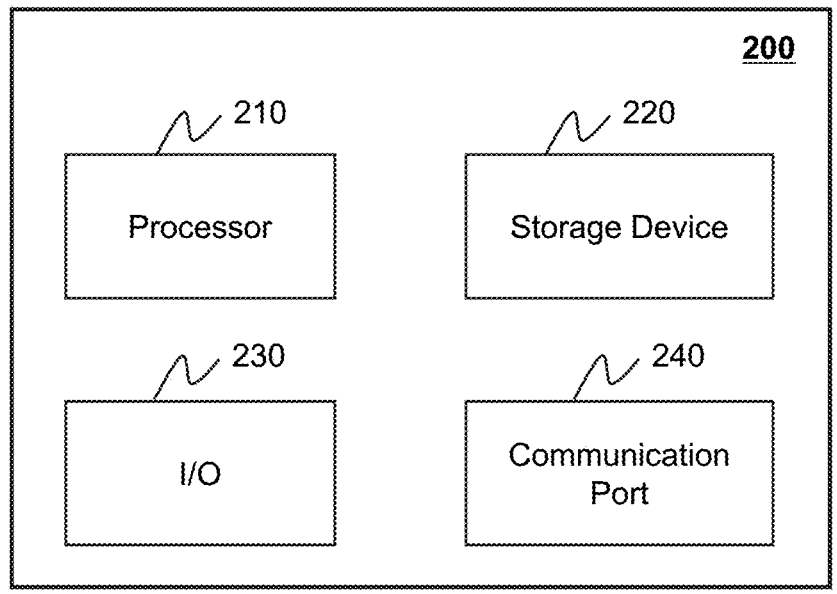
FIG. 2 is a block diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., a processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. For example, the expression "A and/or B" includes only A, only B, or both A and B. The character "/" includes one of the associated listed terms. The term "multiple" or "a/the plurality of" in the present disclosure refers to two or more. The terms "first," "second," and "third," etc., are used to distinguish similar objects and do not represent a specific order of the objects.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Provided herein are systems and components for medical imaging and/or medical treatment. With the development of computer technology and graphic images, medical imaging technology is maturing. As used herein, tomographic images refer to a tomographic image sequence of a specific part of a human body that is generated at intervals along a specific direction using a tomography device. A tomography device refers to a medical device that can be used to perform a scan on an object to obtain tomography images of the object. In some embodiments, the tomography device may include a computed tomography (CT) device, a positron emission tomography (PET) device, a magnetic resonance imaging (MRI) device, a digital breast tomosynthesis (DBT), an ultrasound transmission tomography (UTT) device, or the like, or any combination thereof.

In some embodiments, taking the tomography device of a PET-CT device as an example, the tomography device may include a radiation source (or an excitation source), a detector, a controller, a gantry, or the like, or any combination thereof. During a scan of an object (e.g., a patient or a portion thereof), the tomography device may be caused to perform multiple tomographic scans around a circumference of the object or parallel to a plane of the object at a plurality of angles (several to thousands), and obtain collected data using the detector to acquire radiating or emitting rays passing through the object. The collected data may be reconstructed using a tomography reconstruction algorithm to obtain a three-dimensional (3D) tomographic image of the object. However, during a scan of a patient, a movement of the body of the patient or an internal organ of the patient may result in motion artifacts in the tomographic image(s). The motion artifacts in the tomographic image(s) may need manual correction, which increases the workload and reduces the accuracy of image analysis.

The acquisition of organ movement information may improve the quality of image reconstruction. A large number of soft tissue organs under the skin may be subjected to large-scale nonlinear deformation caused by non-rigid movement (e.g., a physiological motion) of organs such as peristalsis, cardiac motion, respiratory motion, etc. Existing movement detection systems for the internal organ of a patient mainly use a breathing balloon, electrocardiograph (ECG) electrodes, a two-dimensional/three-dimensional (2D/3D) camera, a radar, or other equipment to detect the patient's breathing, heartbeat, and limb movement on the body surface of the patient, which cannot eliminate the influence of the non-rigid movement of internal tissues of the body on tomography image imaging of the patient.

An aspect of the present disclosure relates to systems and methods for tomography imaging using a medical device. The medical device may include an imaging component (e.g., a PET-CT scanner) and at least one laser ultrasonic component. In some embodiments, the system may obtain an ultrasonic signal indicating a movement state of a position of an object (e.g., a position on the surface of the object or a position inside the object) The ultrasonic signal may be acquired by at least one laser ultrasonic component of a medical device. The system may determine, based on the ultrasonic signal, movement information of the position of the object. The system may also obtain, based on the movement information of the position, target image data of the object using the imaging component of the medical device.

Another aspect of the present disclosure relates to systems including a medical device. The medical device may include at least one laser ultrasonic component configured to acquire an ultrasonic signal indicating a movement state of a position of an object. The medical device may also include an imaging component configured to acquire, based on the ultrasonic signal, image data of the object.

According to some embodiments of the present disclosure, an ultrasonic signal generated inside an object may be detected by at least one laser ultrasonic component of a medical device. The ultrasonic signal may be used to determine motion information (e.g., non-rigid movement) of the object. Merely by way of example, the ultrasonic signal may be reconstructed to generate an ultrasonic image of the object, achieving the non-contact ultrasonic imaging of soft tissue, organs, et., of the object. The motion information of the object may be determined based on the ultrasonic image of the object. Further, the motion information of the object may be used to determine one or more scan parameters for performing a scan on the object using an imaging component of the medical device. Alternatively, the motion information of the object may be used to determine one or more reconstruction parameters for image reconstruction. Accordingly, the laser ultrasonic imaging may be associated with the tomography imaging and reconstruction, and the motion information of the object determined based on the ultrasonic imaging may be used to assist the tomography imaging, which can improve the image quality of tomographic images generated using the imaging component. In addition, the at least one laser ultrasonic component may be integrated with the medical device, such that there is no need to detect the movement state of the object using an additional detection device, thereby improving the accuracy of motion detection and imaging.

The following description is provided with reference to exemplary embodiments that the medical device includes an imaging component (e.g., a scanner unless otherwise stated. However, it is understood that it is for illustration purposes only and not intended to limit the scope of the present disclosure. The system and method disclosed herein may be suitable for other applications. Merely by way of example, the medical device may include a radiotherapy device (an image-guided radiotherapy (IGRT) device); the system and method can be used to identify a non-rigid motion (e.g., a physiological motion) for controlling imaging and/or the delivery of a radiation beam in radiotherapy.

Figure 1:
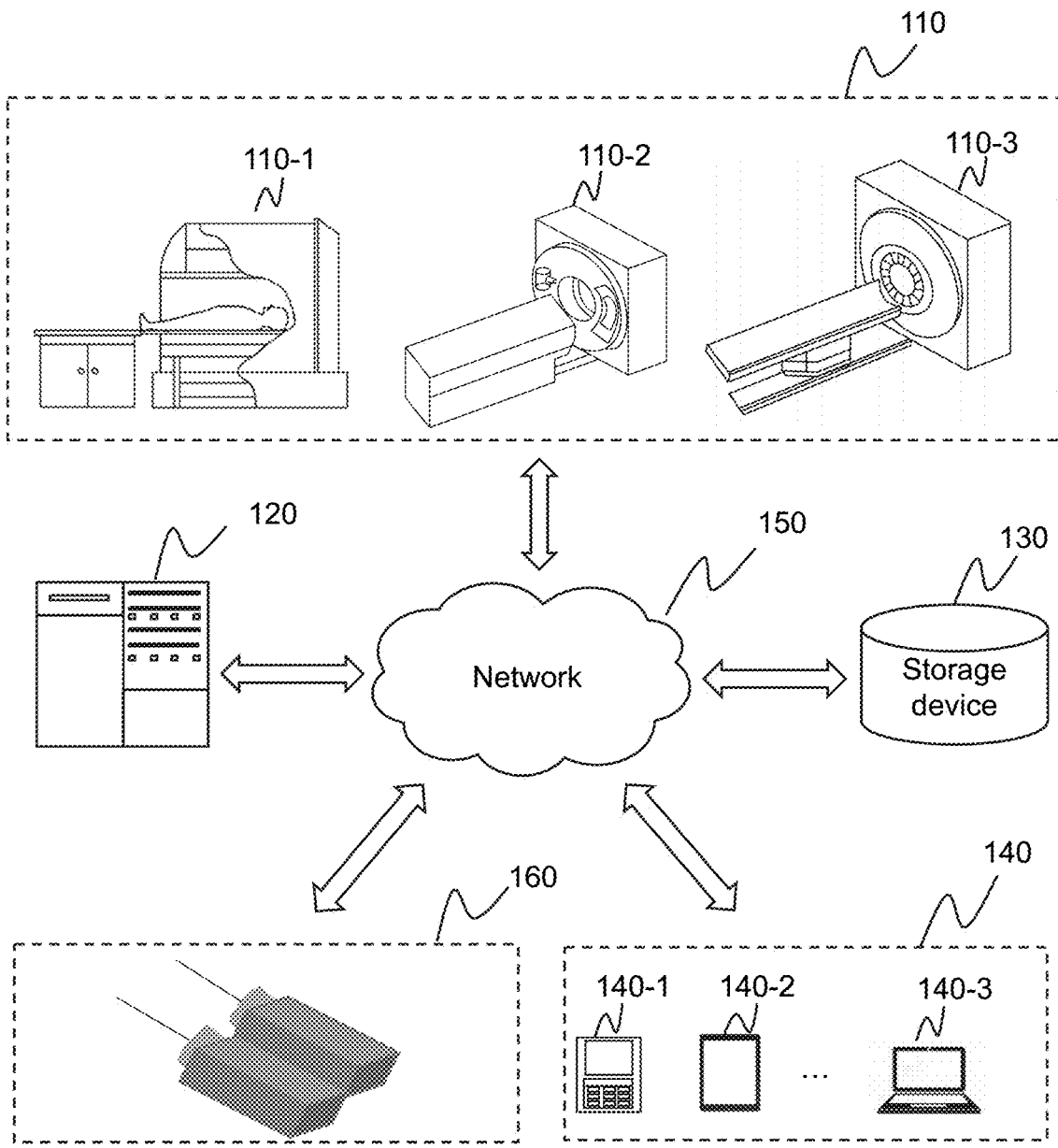
FIG. 1 is a schematic diagram illustrating an exemplary medical system according to some embodiments of the present disclosure.

FIG. 1 is a schematic diagram illustrating an exemplary medical system according to some embodiments of the present disclosure. As shown in FIG. 1, the medical system 100 may include a medical device 110, a processing device 120, a storage device 130, one or more terminals 140, a network 150, and at least one laser ultrasonic component 160 (e.g., one or more laser ultrasonic components 160). The components in the medical system 100 may be connected in one or more of various ways. Merely by way of example, as illustrated in FIG. 1, the medical device 110 may be connected to the processing device 120 through the network 150. As another example, the medical device 110 may be connected to the processing device 120 directly. As a further example, the storage device 130 may be connected to the processing device 120 directly or through the network 150. As still a further example, one or more terminals 140 may be connected to the processing device 120 directly or through the network 150. As still a further example, the at least one laser ultrasonic component 160 may be connected to the processing device 120 directly or through the network 150.

The medical device 110 may generate or provide image data by scanning an object or at least a part of the object. In some embodiments, the medical device 110 may include a medical imaging component, for example, a positron emission tomography (PET) device, a single photon emission computed tomography (SPECT) device, a computed tomography CT device, a magnetic resonance imaging (MRI) device, a radiation therapy (RT) device, or the like, or any combination thereof. In some embodiments, the medical device 110 may include a single-modality scanner. The single-modality scanner may include, for example, a magnetic resonance (MR) scanner 110-1, a computed tomography (CT) scanner 110-2, and/or a positron emission tomography (PET) scanner 110-3. In some embodiments, the medical device 110 may include both the CT scanner 110-2 and the PET scanner 110-3. In some embodiments, image data of different modalities related to the object, such as CT image data and PET image data, may be acquired using different scanners separately. In some embodiments, the medical device 110 may include a multi-modality scanner. The multi-modality scanner may include a positron emission tomography-computed tomography (PET-CT) scanner, a positron emission tomography-magnetic resonance imaging (PET-MRI) scanner, or the like, or any combination thereof. The multi-modality scanner may perform multi-modality imaging simultaneously. For example, the PET-CT scanner may generate structural X-ray CT image data and functional PET image data simultaneously in a single scan. The PET-MRI scanner may generate MRI data and PET data simultaneously in a single scan. In some embodiments, the medical device 110 may include an image-guided radiotherapy (IGRT) device (not shown in FIG. 1). For example, the IGRT device may include a positron emission tomography-radiotherapy (PET-RT) device, or a magnetic resonance imaging-radiotherapy (MRI-RT) device, etc.

Merely by way of example, the medical device 110 may include the PET scanner 110-3. The PET scanner 110-3 may include a gantry with a bore, one or more detection rings (also referred to as detection ring units), etc. The one or more detection rings may be set in the bore of the gantry. Each of the one or more detection rings may include a plurality of detection sub-units Each of the plurality of detection units may include a crystal array. In a PET scanning process, a radiopharmaceutical (also referred to as a radioactive tracer) may be administered to the object, in which the radioactive decay events of the radiopharmaceutical may produce positrons. A positron may interact with a free electron in the human tissue of the object to produce a positron-electron annihilation event and emit two oppositely directed y photons. One or more detection rings may detect the two oppositely directed y photons, and convert the two oppositely directed y photons to electronic signals using a photoelectric component. Further, a coincident event may be determined by amplification, analog-to-digital conversion, energy and time discrimination, or the like, or any combination thereof.

In some embodiments, the object may include a body, a substance, or the like, or any combination thereof. In some embodiments, the object may include a specific portion of a body, such as a head, a thorax, an abdomen, or the like, or any combination thereof. In some embodiments, the object may include a specific organ, such as the esophagus, the trachea, the bronchus, the stomach, the gallbladder, the small intestine, the colon, the bladder, a ureter, the uterus, a fallopian tube, etc. In some embodiments, the object may include a physical model (e.g., a water phantom). In the present disclosure, "object" and "subject" are used interchangeably. In some embodiments, the medical device 110 may include a scanning table. The object may be placed on the scanning table for imaging.

In some embodiments, the medical device 110 may transmit the image data via the network 150 to the processing device 120, the storage device 130, the terminal(s) 140, and/or the at least one laser ultrasonic component 160. For example, the image data may be sent to the processing device 120 for further processing or may be stored in the storage device 130. In some embodiments, the medical device 110 may be configured to scan the object or at least a part of the object in response to a control signal generated by the processing device 120.

The processing device 120 may process data and/or information obtained from the medical device 110, the storage device 130, the terminal(s) 140, and/or the at least one laser ultrasonic component 160. For example, the processing device 120 may obtain an ultrasonic signal indicating a movement state of a position of an object through the at least one laser ultrasonic component 160. The position of the object may be inside the object or on the surface of the object. The processing device 120 may determine, based on the ultrasonic signal, movement information of the position of the object. The processing device 120 may obtain, based on the movement information of the position, target image data of the object using an imaging component of the medical device 110. As another example, the processing device 120 may determine, based on the movement information, a parameter set including one or more scan parameters. The processing device 120 may cause the imaging component of the medical device 120 to perform a scan on the object based on the one or more scan parameters. As yet another example, the processing device 120 may determine, based on the movement information, a parameter set including one or more image reconstruction parameters. The processing device 120 may obtain image data of the object acquired by the imaging component of the medical device 110. The processing device 120 may obtain the target image data based on the image data of the object and the one or more image reconstruction parameters. As further another example, the processing device 120 may generate a target image of the object based on the target image data.

In some embodiments, the processing device 120 may be a single server or a server group. The server group may be centralized or distributed. In some embodiments, the processing device 120 may be local or remote. For example, the processing device 120 may access information and/or data from the medical device 110, the storage device 130, the terminal(s) 140, and/or the at least one laser ultrasonic component 160 via the network 150. As another example, the processing device 120 may be directly connected to the medical device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as illustrated in FIG. 2 or be a portion of the terminal 140.

The storage device 130 may store data, instructions, and/or any other information. In some embodiments, the storage device 130 may store data obtained from the medical device 110, the processing device 120, the terminal(s) 140, and/or the at least one laser ultrasonic component 160. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. In some embodiments, the storage device 130 may be implemented on a cloud platform as described elsewhere in the disclosure. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140, the at least one laser ultrasonic component 160, etc.). One or more components in the medical system 100 may access the data or instructions stored in the storage device 130 via the network 150. In some embodiments, the storage device 130 may be part of the processing device 120.

The terminal(s) 140 may be connected to and/or communicate with the medical device 110, the processing device 120, and/or the storage device 130. For example, the terminal(s) 140 may obtain a processed image from the processing device 120. As another example, the terminal(s) 140 may obtain scan data acquired by the medical device 110 and transmit the scan data to the processing device 120 to be processed. In some embodiments, the terminal(s) 140 may include a mobile device 140-1, a tablet computer 140-2, a laptop computer 140-3, or the like, or any combination thereof. For example, the mobile device 140-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate the exchange of information and/or data for the medical system 100. In some embodiments, one or more components of the medical system 100 (e.g., the medical device 110, the processing device 120, the storage device 130, the terminal(s) 140, the at least one laser ultrasonic component 160, etc.) may communicate information and/or data with one or more other components of the medical system 100 via the network 150. For example, the processing device 120 may obtain image data from the medical device 110 via the network 150. As another example, the processing device 120 may obtain user instruction(s) from the terminal(s) 140 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, server computers, or the like, or a combination thereof. For example, the network 150 may include a wireline network, an optical fiber network, a telecommunication network, a local area network, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points, through which one or more components of the medical system 100 may be connected to the network 150 to exchange data and/or information.

The at least one laser ultrasonic component 160 may be configured to acquire an ultrasonic signal generated inside the object using laser ultrasonic detection. Laser ultrasonic detection is a manner of non-contact and long-distance non-destructive detection. When a laser with certain energy (i.e., an energy pulse or laser pulse) irradiates on the surface of an object, a part of the energy may be expressed in the form of heat energy and wave energy. The transient thermal interaction between a high-energy laser pulse and the object surface may cause the generation of strain and stress field on the object surface through the thermoelastic effect, and corresponding particle fluctuation may be generated and produce the ultrasonic signal inside the object. Then, the internal structure of the object may be imaged by detecting the ultrasonic signal emitted from the inside of the object.

In some embodiments, each of the at least one laser ultrasonic component 160 may include a first laser source and a second laser source. The first laser source may be configured to emit an energy pulse to the object for generating the ultrasonic signal, and also be referred to as a laser emission source. The second laser source may be configured to detect the ultrasonic signal for further processing, and also be referred to as a laser ultrasonic detection source. For example, the ultrasonic signal may be processed for determining scan parameter(s) according to which a medical scan of the object is performed, positioning the object before performing the medical scan, controlling the process of the medical scan of the object, performing the medical scan of the object according to a retrospective gating technique, determining image reconstruction parameter(s), or the like, or any combination thereof. In some embodiments, the second laser source may include a continuous laser, such as a continuous wave (CW) laser. For example, the second laser source may include a laser doppler vibrometer. The power of each of the first laser source and the second laser source may be less than a preset power (e.g., 0.4 megawatts). The preset power may be associated with a safety need of the object, e.g., a power below the preset power may be safe to the eyes, the skin of a patient, etc. For example, the wavelength of the first laser source or the second laser source may be 1400 nanometers (nm)-1600 nm. As another example, the wavelength of the first laser source or the second laser source may be 1500 nm-1600 nm. As yet another example, the wavelength of the first laser source may be 1540 nm, and the wavelength of the second laser source may be 1550 nm.

In some embodiments, since the ultrasonic signal generated inside the object excited by the first laser source has a limited action range of photoacoustic effect, the first laser source and the second laser source may be set to be confocal, which ensures the detection range of the second laser source covers a generation region of the ultrasonic signal. As used herein, the confocal setting refers to that a first laser emitted by the first laser source and a second laser emitted by the second laser source are guided to a same position. For example, the first laser source and the second laser source may be arranged to emit the first laser and the second laser directing to the same position. As another example, the first laser source and the second laser source may be arranged to emit the first laser and the second laser directing two steering mirrors respectively. The two steering mirrors may guide the first laser and the second laser respectively to reach the same position. It should be noted that any other light guide manner can be used for achieving the confocal setting of the first laser source and the second laser source, which is not limited herein.

Figure 3:
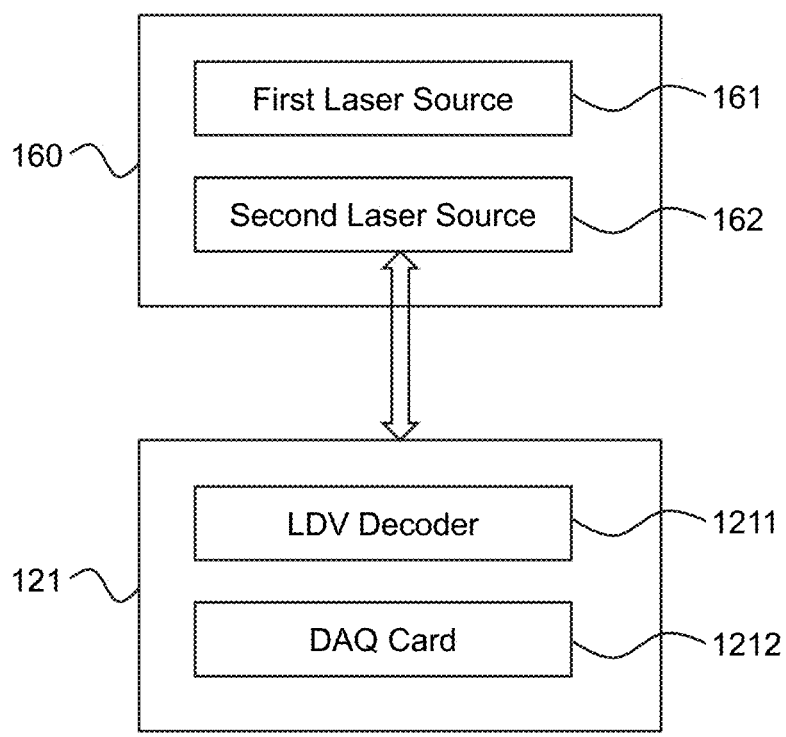
FIG. 3 is a block diagram illustrating exemplary hardware and/or software components of an exemplary laser ultrasonic component and an exemplary laser velocimetry detection component according to some embodiments of the present disclosure.

In some embodiments, the at least one laser component 160 may be connected with one or more components of the medical system 100 or communicate with one or more components (e.g., the processing device 120, the storage device 130, the terminal 140) of the medical system 100 via the network 150. For example, as shown in FIG. 3, each of the at least one laser ultrasonic component 160 may include a first laser source 161 and a second laser source 162. The first laser source 161 may be coupled with the second laser source 162. The first laser source 161 may emit a high-energy laser pulse to the object for generating an ultrasonic signal inside the object. The second laser source 162 may detect the ultrasonic signal generated inside the object. In some embodiments, the medical system 100 may include a laser velocimetry detection component 121 that communicates with the second laser source 162 (e.g., the second laser source 162 may transmit the ultrasonic signal to the laser velocimetry detection component 121 for processing). For example, the first laser source 161 may emit a high-energy laser pulse to the object and cause the object to vibrate and generate an initial ultrasonic signal. The initial ultrasonic signal may be reflected in the object to generate the ultrasonic signal. The second laser source 162 may detect the ultrasonic signal by detecting vibrations of the object that are generated by the ultrasonic signal. Since the vibrations of the object, the frequency of a lightwave signal reflected by the object may change. The second laser source 162 may emit a laser velocimetry pulse to a detection area of the object and detect the laser velocimetry pulse reflected by the object for determining a frequency change of the reflected laser velocimetry pulse. Further, the second laser source 162 may transmit the ultrasonic signal and the frequency of the reflected laser velocimetry pulse to the laser velocimetry detection component 121.

The laser velocimetry detection component 121 may include a laser doppler velocimetry (LDV) decoder 1211 and a data acquisition (DAQ) component (e.g., a DAQ card) 1212. The LDV decoder 1211 may be communicatively connected with the second laser source 162. The LDV decoder 1211 may be configured to determine the frequency change of the reflected lightwave (e.g., reflected laser velocimetry pulse) from the object and convert the frequency change to quantitative data (e.g., a vibration displacement) of the object that reflects movement information of the object. The DAQ component 1212 may be communicatively connected with the LDV decoder 1211. The DAQ component 1212 may be configured to store the quantitative data of the object and the ultrasonic signal of the object. Further, the DAQ component 1212 may transmit the quantitative data (e.g., the vibration displacement) of the object to the processing device 120 for subsequent processing. In some embodiments, the laser velocimetry detection component 121 may be integrated into one or more components of the medical system 100. For example, the laser velocimetry detection component 121 may be part of the processing device 120. That is, the functions of the LDV decoder 1211 and the DAQ component 1212 may be achieved by the processing device 120. As another example, the LDV decoder 1211 may be a part of the processing device 120, and the DAQ component 1212 may be a part of the storage device 130. That is, the function of the LDV decoder 1211 may be achieved by the processing device 120, and the function of the DAQ component 1212 may be achieved by the storage device 130. As yet another example, the second laser source 162 and the laser velocimetry detection component 121 may be set integrally or separately.

In some embodiments, the at least one laser ultrasonic component 160 may be disposed on various suitable positions for obtaining the motion information of the object. For instance, the at least one laser ultrasonic component 160 may be arranged on a component of the medical device 110 (e.g., a PET scanner). For example, the PET scanner 110-3 may include a PET scanner with a short axial field of view (FOV). The short axial FOV refers to that the length of the axial FOV of the PET scanner 110-3 along an axis direction of the PET scanner 110-3 is less than a preset threshold (e.g., 1 meter, 0.7 meters, 0.5 meters, etc.). The axis direction of the PET scanner may be a direction that the scanning table enters the bore or a longitude direction of the table. The at least one laser ultrasonic component 160 may be disposed at an end of the bore of the PET scanner 110-3 with the short axial FOV. For instance, if there are two laser ultrasonic components 160, the two laser ultrasonic components 160 may be disposed at two ends of the bore of the PET scanner 110-3 with the short axial FOV, respectively. As another example, the at least one laser ultrasonic component 160 may be supported by a holder of the imaging component of the medical device 110. The holder may be arranged on the scanning table of the medical device 110. As yet another example, the imaging component (e.g., the PET scanner 110-3) of the medical device 110 may include a PET scanner with a long axial FOV. The long axial FOV refers to that that the length of the axial FOV of the PET scanner 110-3 along the axis direction of the PET scanner 110-3 is greater than a preset threshold (e.g, 1 meter, 0.7 meters, 0.5 meters, etc.). The at least one laser ultrasonic component 160 may be disposed between at least two detection rings of the PET scanner 110-3. For instance, if the PET scanner 110-3 includes two detection rings, the at least one laser ultrasonic component 160 may be disposed between the two detection rings of the PET scanner 110-3. Accordingly, the at least one laser ultrasonic component 160 may be disposed properly without affecting the detection effect of the detection ring(s). In some embodiments, although the at least one laser ultrasonic component 160 is separately arranged with the medical device 110 in FIG. 1, the at least one laser ultrasonic component 160 may be part of the medical device 110. More descriptions of the laser ultrasonic component 160 may be found elsewhere in the present disclosure (e.g., FIGS. 4 and 5 and the descriptions thereof).

In some embodiments, a count of the detection ring(s) of the PET scanner 110-3, a count of the at least one laser ultrasonic component 160, and/or the position of the at least one laser ultrasonic component 160 may be set or adjusted according to different clinical situations, which is not limited herein. In some embodiments, a detection range of the detection ring(s) of the PET scanner 110-3 may cover a scanning range of the object to be scanned. A detection range of the at least one laser ultrasonic component 160 may cover the detection range of the detection ring(s).

It should be noted that the above description regarding the medical system is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical system may include one or more additional components, and/or one or more components of the medical system described above may be omitted. In some embodiments, a component of the medical system may be implemented on two or more sub-components. Two or more components of the medical system may be integrated into a single component.

FIG. 2 is a schematic diagram illustrating exemplary hardware and/or software components of an exemplary computing device according to some embodiments of the present disclosure. The computing device 200 may be configured to implement any component of the medical system. For example, the medical device 110, the terminal 140, the processing device 120, and/or the storage device 130 may be implemented on the computing device 200. Although only one such computing device is shown for convenience, the computer functions relating to the medical system as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal 140 and/or the storage device 130. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the medical device 110, the terminal 140, the storage device 130, the at least one laser ultrasonic component 160, or any other component of the medical system 100. In some embodiments, the storage device 220 may include a mass storage device, a removable storage device, a volatile read-and-write memory, a read-only memory (ROM), or the like, or any combination thereof. For example, the mass storage device may include a magnetic disk, an optical disk, a solid-state drive, a mobile storage device, etc. The removable storage device may include a flash drive, a floppy disk, an optical disk, a memory card, a ZIP disk, a magnetic tape, etc. The volatile read-and-write memory may include a random access memory (RAM). The RAM may include a dynamic RAM (DRAM), a double date rate synchronous dynamic RAM (DDR-SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 220 may store one or more programs and/or instructions to perform exemplary methods described in the present disclosure.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, a camera capturing gestures, or the like, or a combination thereof. Exemplary output devices may include a display device, a loudspeaker, a printer, a projector, a 3D hologram, a light, a warning light, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the medical device 110, the terminal 140, the storage device 130, the at least one laser ultrasonic component 160, or any external devices (e.g., an external storage device, or an image/data processing workstation). The connection may be a wired connection, a wireless connection, or a combination of both that enables data transmission and reception. The wired connection may include an electrical cable, an optical cable, a telephone wire, or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

In some embodiments, the computing device 200 may further include a bus (not shown) configured to achieve the communication between the processor 210, the storage device 220, the I/O 230, and/or the communication port 240. The bus may include hardware, software, or both, which decouple the components of the computing device 200 to each other. The bus may include at least one of a data bus, an address bus, a control bus, an expansion bus, or a local bus. For example, the bus may include an accelerated graphics port (AGP) or other graphics bus, an extended industry standard architecture (EISA) bus, a front side bus (FSB), a hyper transport (HT) interconnection, an industry standard architecture (ISA) bus, a front side bus (FSB), an Infiniband interconnection, a low pin count (LPC) bus, a storage bus, a micro channel architecture (MCA) bus, a peripheral component interconnect (PCI) bus, a PCI-Express (PCI-X) bus, a serial advanced technology attachment (SATA) bus, a video electronics standards association local bus (VLB) bus, or the like, or any combination thereof. In some embodiments, the bus may include one or more buses. Although specific buses are described, the present disclosure may consider any suitable bus or interconnection.

Figure 4:
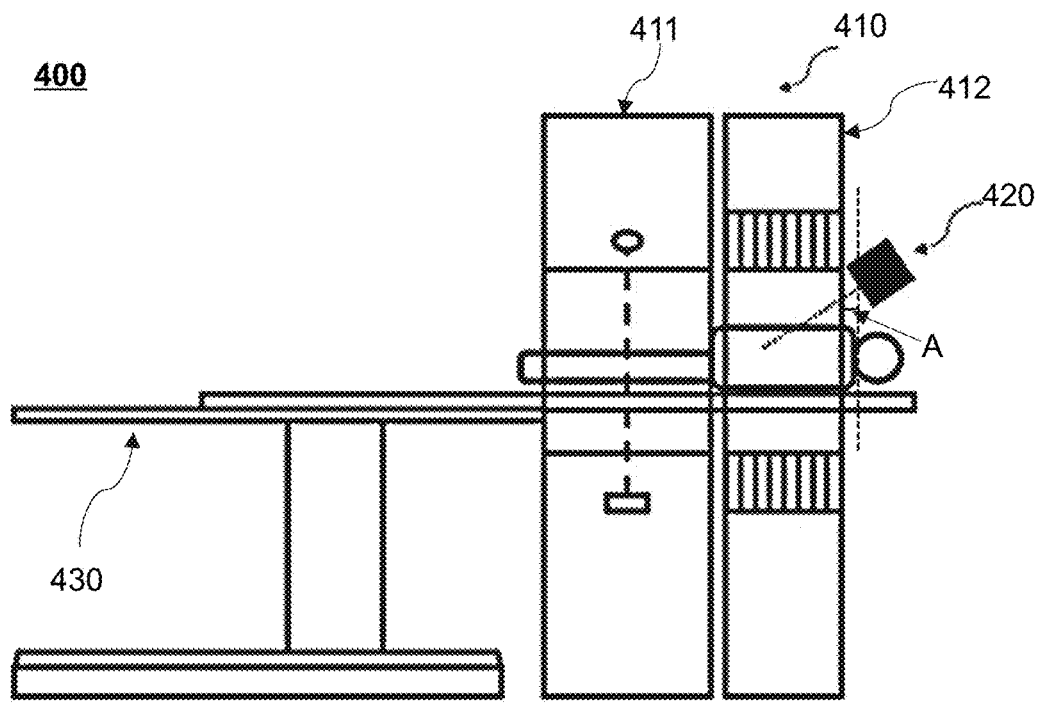
FIGS. 4 and 5 are schematic diagrams illustrating exemplary medical devices according to some embodiments of the present disclosure.

FIG. 4 is a schematic diagram illustrating an exemplary medical device according to some embodiments of the present disclosure. As shown in FIG. 4, the medical device 400 may include an imaging component (e.g., a PET-CT scanner) 410, a laser ultrasonic component 420, a table 430, etc. The imaging component 410 may be configured to scan an object placed on the table 430 and/or at least a part of the object, and acquire corresponding scan data (also referred to as image data). The laser ultrasonic component 420 may be configured to acquire an ultrasonic signal indicating motion information (e.g., a physiological motion) of the object. For example, the ultrasonic signal may indicate a movement state of a position of the object (e.g., a position on the surface of the object and/or inside the object).

In some embodiments, the imaging component 410 may include a CT scanner 411 and a PET scanner 412. The PET scanner 410 may include at least one detection ring disposed in a bore of the PET scanner 412. The laser ultrasonic component 420 may be disposed above the object. For example, the laser ultrasonic component 420 may be disposed at an end of the bore of the PET scanner 412 (e.g., an end away from the CT scanner 411 as shown in FIG. 4). As another example, the laser ultrasonic component 420 may be disposed at an end between a bore of the CT scanner 411 and the bore of the PET scanner 412. As still another example, the laser ultrasonic component 420 may be disposed at an end of the bore of the CT scanner 411 away from the PET scanner 410. As still another example, the laser ultrasonic component 420 may be disposed inside the bore the CT scanner 411. In some embodiments, the laser ultrasonic component may be supported by a holder set on the table 430. The holer may be fixed or movable with respect to the table. In some embodiments, the laser ultrasonic component 420 may be arranged along a reference axis that forms a tilting angle A with a vertical line. The vertical line refers to a line perpendicular to the horizontal plane (parallel to the ground). The ultrasonic component 420 being arranged along the reference axis refers to that a laser beam emitted by a first laser source (similar to the first laser source 161) or a second laser source (similar to the second laser source 162) of the laser ultrasonic component 420 is parallel to the reference axis. The tilting angle A may be less than a preset angle, such that the laser beam emitted by the first laser source and/or the second laser source may not be affected (e.g., shielded) by a part of the object (e.g., hair of a patient), improving a signal to noise ratio (SNR) of the ultrasonic signal detected by the laser ultrasonic component 420. In some embodiments, the laser ultrasonic component 420 may be integrated with a laser velocimetry detection component (e.g., the laser velocimetry detection component 121). Alternatively, the laser velocimetry detection component may be disposed separately with the laser ultrasonic component 420. For example, the laser velocimetry detection component may be integrated with a processing device (e.g., the processing device 120).

Figure 5:
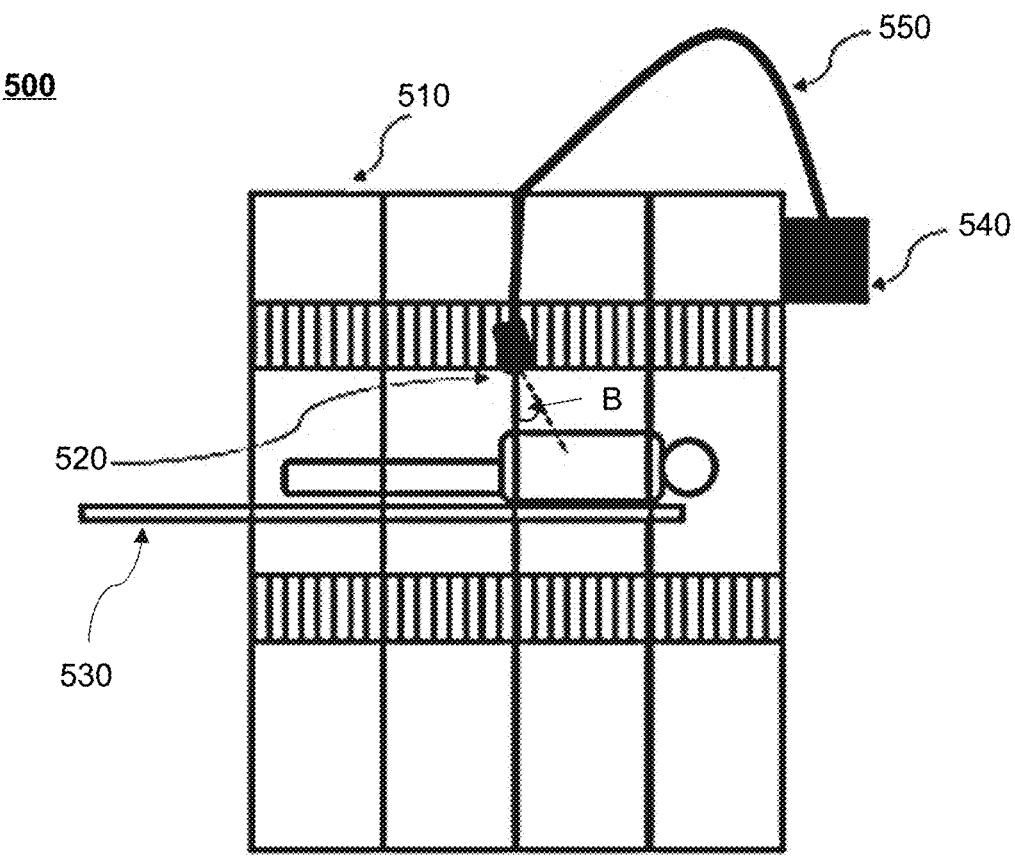

FIG. 5 is a schematic diagram illustrating an exemplary medical device according to some embodiments of the present disclosure. As shown in FIG. 5, the medical device 500 may include an imaging component (e.g., PET scanner with a long axial FOV) 510, a laser ultrasonic component 520, a table 530, a laser velocimetry detection component 540, etc. The imaging component 510 may be configured to scan an object placed on the table 530 and/or at least a part of the object, and acquire corresponding scan data. The laser ultrasonic component 520 may be configured to acquire an ultrasonic signal indicating motion information (e.g., a physiological motion) of the object. For example, the ultrasonic signal may indicate a movement state of a position of the object (e.g., a position on the surface of the object or inside the object). The laser velocimetry detection component 540 may be configured to process the ultrasonic signal to determine the motion information of the object.

In some embodiments, as a position of the laser ultrasonic component 520 affects the SNR of the ultrasonic signal detected by the laser ultrasonic component 520, the laser ultrasonic component 520 may need to be arranged to satisfy an SNR need. For example, if the laser ultrasonic component 520 is disposed at a tilting angle greater than the preset angle described in FIG. 4, the probability of the light signal reflecting back to its original path may be relatively low, resulting in low SNR of the ultrasonic signal detected by the laser ultrasonic component 520. Accordingly, when the PET scanner 510 is with the long axial FOV, the laser ultrasonic component 520 and the laser velocimetry detection component 540 may be disposed separately. As shown in FIG. 5, the imaging component 510 may include four detection rings. The laser ultrasonic component 520 may be disposed between two adjacent detection rings of the imaging component 510 at a tilting angle B and above the object. The titling angle B may be less than a preset angle (e.g., 10 degrees, 15 degrees, 20 degrees, etc.). The laser velocimetry detection component 540 may be disposed on an end of a bore of the imaging component 510. The laser velocimetry detection component 540 may be connected with the laser ultrasonic component 520 via a connection (e.g., an optical fiber) 550.

It should be noted that the medical devices 400 and 500 are provided for illustration purposes, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, in FIG. 5, the laser velocimetry detection component 540 may be disposed at any other position of the medical device 500. For example, the laser velocimetry detection component 540 may be disposed on a holder of the medical device 500. As another example, the laser velocimetry detection component 540 may be disposed above the bore of the imaging component 510. As yet another example, the velocimetry detection component 540 may be disposed beneath the object. In some embodiments, the laser velocimetry detection component 540 may be integrated into other components (e.g., the processing device 120, the storage device 130, etc.) of the medical system 100. The laser velocimetry detection component 540 may communicate with the laser ultrasonic component 520 via the network 150. In some embodiments, the tilting angle A or the tilting B may be adjusted. For example, the processing device 120 may adjust the titling angle A (or the tilting angle B) by controlling a driver component to move or rotate the laser ultrasonic component 420 (or the laser ultrasonic component 520) or steering mirrors corresponding thereof.

Figure 6:
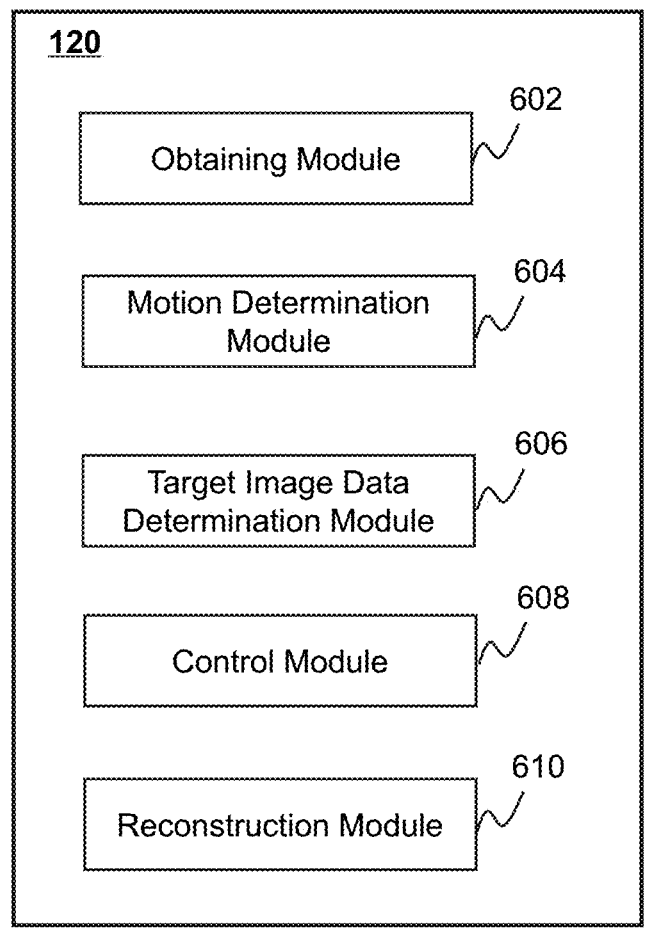
FIG. 6 is a block diagram illustrating an exemplary processing device according to some embodiments of the present disclosure.

FIG. 6 is a block diagram illustrating an exemplary processing device according to some embodiments of the present disclosure. In some embodiments, the processing device 120 may be in communication with a computer-readable storage medium (e.g., the storage device 130 illustrated in FIG. 1, or the storage device 220 illustrated in FIG. 2) and may execute instructions stored in the computer-readable storage medium. The processing device 120 may include an obtaining module 602, a motion determination module 604, a target image data determination module 606, a control module 608, and a reconstruction module 610.

The obtaining module 602 may be configured to acquire data from one or more components of the medical system 100. In some embodiments, the obtaining module 602 may obtain an ultrasonic signal indicating a movement state of a position of an object. The ultrasonic signal may be acquired before a scan of the object or during the scan of the object. For example, the obtaining module 602 may obtain the ultrasonic signal from at least one laser ultrasonic component (e.g. the at least one laser ultrasonic component 160, the laser ultrasonic component 420, the laser ultrasonic component 430, etc.). As another example, the obtaining module 602 may obtain the ultrasonic signal from a storage device (e.g., the storage device 130, the storage device 220, etc.). In some embodiments, the obtaining module 602 may obtain scan data (i.e., image data) of the object acquired during a scan of the object. For example, the obtaining module 602 may obtain the image data of the object from the medical device 110. As another example, the obtaining module 602 may obtain the image of the object from a storage device (e.g., the storage device 130, the storage device 220, etc.). More descriptions regarding the obtaining of the ultrasonic signal and/or the image data of the object may be found elsewhere in the present disclosure (e.g., FIG. 7 and relevant descriptions thereof).

The motion determination module 604 may be configured to determine, based on the ultrasonic signal, movement information (e.g., cardiac motion data and/or the respiratory motion data) and/or structural characteristic information of the object. For example, the motion determination module 604 may generate, based on the ultrasonic signal, a motion curve related to the position of the object. The motion determination module 604 may determine, based on the motion curve, the movement information of the object (e.g., movement information of the position of the object). As another example, the motion determination module 604 may generate, based on the ultrasonic signal, a gating signal. The gating signal may include a cardiac gating signal, a respiratory gating signal, etc., that can be used to generate a control signal for controlling the scan of the object using a gating technique. As further another example, the motion determination module 604 may generate, based on the ultrasonic signal, an ultrasonic image related to the position of the object using a reconstruction algorithm. The motion determination module 604 may determine, based on the ultrasonic image, the structural characteristic information of the object. More descriptions regarding the determination of the movement information and/or the structural characteristic information of the object may be found elsewhere in the present disclosure (e.g., FIG. 7 and relevant descriptions thereof).

The target image data determination module 606 may be configured to determine target image data of the object. In some embodiments, the target image data determination module 606 may determine the target image data of the object based on initial image data acquired during the scan of the object. For example, the target image data determination module 606 may determine, based on the movement information, a parameter set including one or more scan parameters. The target image data determination module 606 may transmit the one or more scan parameters to the control module 608 for generating a control signal to cause an imaging component of a medical device (e.g., the medical device 110) to perform a scan on the object based on the one or more scan parameters. The target image data determination module 606 may obtain the target image data of the object by causing the imaging component to perform the scan on the object. As another example, the target image data determination module 606 may determine, based on the movement information, a parameter set including one or more image reconstruction parameters. The target image data determination module 606 may obtain (or determine) image data of the object by causing the imaging component to perform a scan on the object. The target image data determination module 606 may obtain (or determine) the target image data of the object based on the image data of the object and the one or more image reconstruction parameters. As still another example, the target image data determination module 606 may obtain the target image data of the object by triggering the imaging component to perform a scan according to the movement information. As further another example, the target image data determination module 606 may obtain initial image data of the object by causing the imaging component to perform a scan on the object. The target image data determination module 606 may obtain the target image data of the object based on the initial image data of the object and the movement information. More descriptions of the determination of the target image data of the object may be found elsewhere in the present disclosure (e.g., FIG. 7 and relevant descriptions thereof).

The control module 608 may be configured to generate a control signal for controlling the medical device to scan the object or a portion thereof. In some embodiments, the control module 608 may generate the control signal based on the movement information of the object. For example, the control module 608 may generate the control signal using a gating technique. The gating technique may include a cardiac gating and a respiratory gating. In response to the control signal, the imaging component of the medical device may be directed to scan the object or a portion thereof. In some embodiments, the control module 608 may generate a control signal for controlling the at least one laser ultrasonic component of the medical device to detect the ultrasonic signal.

The reconstruction module 610 may be configured to generate a target image of the object based on the target image data. For example, the reconstruction module 610 may reconstruct the target image using one or more reconstruction algorithms. The one or more reconstruction algorithms may include a 2D Fourier transform technique, a back projection technique (e.g., a convolution back projection technique, a filtered back projection technique), an iteration reconstruction technique, etc. Examples of iterative reconstruction techniques may include a simultaneous algebraic reconstruction technique (SART), a simultaneous iterative reconstruction technique (SIRT), an ordered subset convex technique (OSC), ordered subset maximum likelihood methodologies, an ordered subset expectation maximization (OSEM) methodology, an adaptive statistical iterative reconstruction technique (ASIR) methodology, a least squares QR methodology, an expectation maximization (EM) methodology, an OS-separable paraboloidal surrogates technique (OS-SPS), an algebraic reconstruction technique (ART), a Kacsmarz reconstruction technique, or any other iterative reconstruction technique or methodology that meets application-specific requirements. In some embodiments, the reconstruction module 610 may generate an initial image of the object based on the target image data of the object. The reconstruction module 60 may generate the target image of the object by correcting the initial image of the object based on the movement information of the object.

It should be noted that the above descriptions of the processing device 120 are provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. In some embodiments, the processing device 120 may include one or more other modules. For example, the processing device 120 may include a storage module to store data generated by the modules in the processing device 120. In some embodiments, any two of the modules may be combined as a single module, and any one of the modules may be divided into two or more units.

Figure 7:
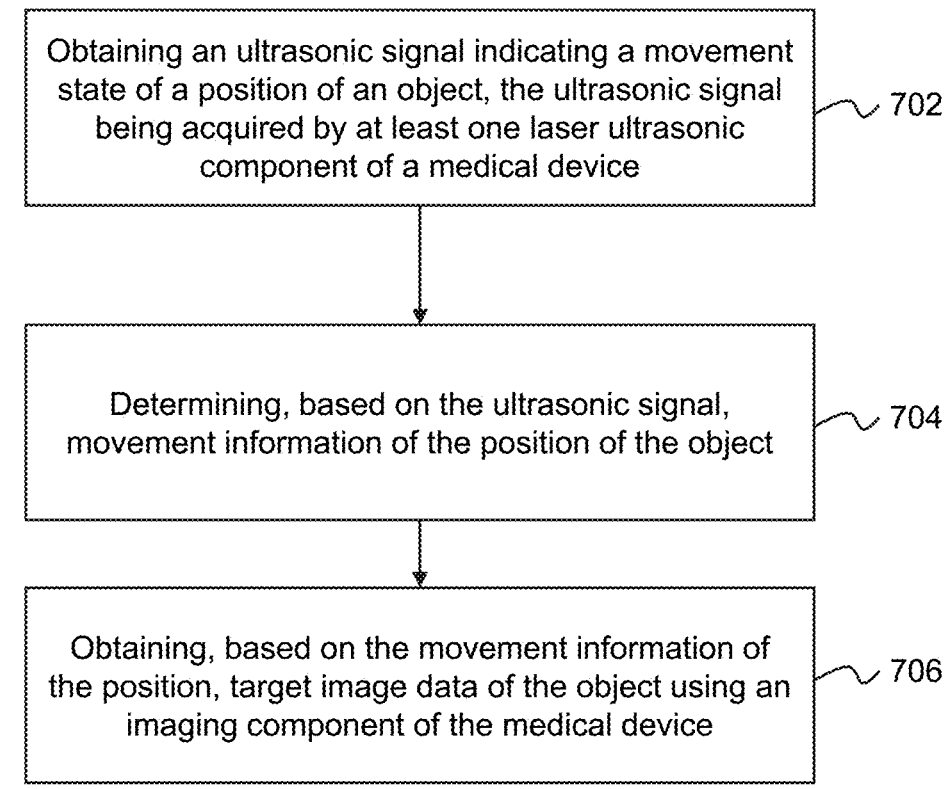
FIG. 7 is a flowchart illustrating an exemplary process for obtaining target image data of an object according to some embodiments of the present disclosure.

FIG. 7 is a flowchart illustrating an exemplary process for obtaining target image data of an object according to some embodiments of the present disclosure. Process 700 may be implemented in the medical system 100 illustrated in FIG. 1. For example, the process 700 may be stored in the storage device 130 and/or the storage device 220 in the form of instructions (e.g., an application), and invoked and/or executed by the processing device 120 (e.g., the processing device 120 illustrated in FIG. 1, or one or more modules in the processing device 120 illustrated in FIG. 6). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 702, the processing device 120 (e.g., the obtaining module 602) may obtain an ultrasonic signal indicating a movement state of a position of an object.

In some embodiments, the ultrasonic signal may be acquired by at least one laser ultrasonic component of a medical device (e.g., the at least one laser ultrasonic component 160 of the medical device 110, the laser ultrasonic component 420 of the medical device 400, or the laser ultrasonic component 520 of the medical device 500). The medical device may also include an imaging component configured to perform a medical scan of the object. In some embodiments, the ultrasonic signal may be acquired when the object is placed on a table of the medical device and in an examination space (e.g., a bore of the imaging component) of the medical device. In some embodiments, the ultrasonic signal may be acquired during a scan of the object using the imaging component of the medical device. In some embodiments, the ultrasonic signal may be acquired before the scan of the object using the imaging component. In some embodiments, the processing device 120 may obtain the ultrasonic signal directly from the at least one laser ultrasonic component. Alternatively, the at least one laser ultrasonic component may store the ultrasonic signal in a storage device (e.g., the storage device 130, the storage device 220, or the DAQ component 1212). The processing device 120 may obtain the ultrasonic signal from the storage device.

In some embodiments, the movement state of the position of the object may include a state of a non-rigid motion (e.g., a physiological motion such as a cardiac motion or a respiratory motion), a rigid motion, etc., of the position of the object. As used herein, the position of the object refers to a physical point (that has a certain area or volume less than a threshold) or a region (that has a certain area or volume exceeding a threshold) on the surface of the object or a position inside the object. For example, if the movement includes the respiratory motion, the position of the object may include a position on the surface of the skin above the sternum of the object which can reflect ups and downs of the sternum. As another example, if the movement includes the cardiac motion, the position of the object may include a position on the heart of the object.

During the acquisition of the ultrasonic signal, a first laser source (e.g. the first laser source 161) and a second laser source (e.g., the second laser source 162) of at least one laser ultrasonic component may be arranged to be confocal at the position of the object to acquire the ultrasonic signal. Alternatively, the ultrasonic signal may indicate a movement state of a region (e.g., an organ such as a breast, the heart, a lung, the stomach, the gallbladder, the small intestine, the colon, etc) of the object.

In a case that there is only a laser ultrasonic component in the medical device, during the acquisition of the ultrasonic signal, the first laser source and the second laser source of the laser ultrasonic component may perform the detection on a region of the object by scanning multiple points in the region of the object. Two adjacent points of the multiple points may be overlapped with each other or be separated by a distance (e.g., 0.5 millimeters (mm), 1 mm, etc.)

In the case that there are two or more laser ultrasonic components in the medical device, during the acquisition of the ultrasonic signal, detection ranges of the laser ultrasonic components may be arranged to cover the region of the object. Each of the laser ultrasonic components may correspond to different portions (or points) of the region of the object.

In some embodiments, a detection range of the at least one laser ultrasonic component may be set to cover a scanning range of the imaging component. The first laser source of the at least one laser ultrasonic component may emit a first laser pulse to the scanning range (e.g., position(s) of the object). The object may generate the ultrasonic signal in response to the first laser pulse. The second laser source of the at least one laser ultrasonic component may detect the ultrasonic signal by emitting a second laser pulse to the scanning range.

In 704, the processing device 120 (e.g., the motion determination module 604) may determine, based on the ultrasonic signal, movement information of the position of the object.

In some embodiments, the movement information of the position of the object may reflect accurate cardiac motion data and/or respiratory motion data of the object, which can facilitate to reduce or avoid motion artifacts (e.g., cardiac motion artifacts or respiratory motion artifacts) in a reconstructed image, and/or controlling the scan of the object. The movement information of the position of the object may include non-rigid motion information such as a motion intensity, a motion frequency, a motion amplitude, a motion speed, a motion cycle, a motion phase, or the like, or any combination of an organ of the object during breathing, heartbeat, or peristalsis (e.g., peristalsis of a tissue of the object at irregular times) of the object. In some embodiments, the processing device 120 may determine structural characteristic information of the object based on the ultrasonic signal. The structural characteristic information of the object may include the size of the object (e.g., a volume of the heart), a location (e.g., a real-time location) of the position of the object, or the like, or any combination thereof.

In some embodiments, the movement information may be reflected in a form of an ultrasonic image, a motion curve, a gating signal, etc., related to the position of the object. For example, the processing device 120 may generate, based on the ultrasonic signal, the motion curve related to the position of the object. The processing device 120 may determine, based on the motion curve, the movement information of the position of the object. For instance, the motion curve may be similar to an electrocardiograph (ECG) curve that shows a plurality of cardiac cycles and different phases of a cardiac cycle. As another example, the processing device 120 may generate, based on the ultrasonic signal, a gating signal. The gating signal may include a cardiac gating signal, a respiratory gating signal, etc., that can be used to generate a control signal for controlling the scan of the object using a gating technique. The gating technique may be used for synchronization of signal (e.g., an MR signal, a PET signal) acquisition to the cardiac and/or respiratory cycle.

In some embodiments, the structural characteristic information of the object may be reflected in a form of an ultrasonic image. For example, the processing device 120 may generate, based on the ultrasonic signal, the ultrasonic image related to the position of the object using a reconstruction algorithm (e.g., a 2D reconstruction algorithm, a 3D reconstruction algorithm, etc.). The ultrasonic image may include a 2D ultrasonic image, a 3D ultrasonic image, etc., related to the position of the object. For example, the processing device 120 may generate the 2D ultrasonic image by performing operations including beam synthesis, filtering, frame correlation, or the like, or any combination thereof, on the ultrasonic signal. As another example, the processing device 120 may perform data processing on the digitally stored 2D ultrasonic images. The processing device 120 may generate the 3D ultrasonic image based on the processed 2D ultrasonic image and a reference perspective stereo image (e.g., a model image). The processing device 120 may determine, based on the ultrasonic image, the movement information at the position of the object.

In 706, the processing device 120 (e.g., the obtaining module 602, the target image data determination module 606, or the control module 608) may obtain, based on the movement information of the position, target image data of the object using an imaging component of the medical device.

In some embodiments, the processing device 120 may determine, based on the movement information, a parameter set including one or more scan parameters. The processing device 120 may obtain the target image data of the object by causing the imaging component to perform the scan on the object based on the one or more scan parameters. Exemplary scan parameters may include a scan range (e.g., including a scan center and a scanning diameter), a scan frequency (e.g., including gating information), a scan thickness (i.e., a thickness of a scan slice), a scan spacing (i.e., a distance of two scan slices), or the like, or any combination thereof, more descriptions of which may be found elsewhere in the present disclosure (e.g., FIG. 7 and relevant descriptions thereof). For example, the ultrasonic signal may be acquired before a scan of the object and indicate a movement state and/or structural characteristic information of the object before the scan of the object. In such cases, the processing device 120 may determine, based on the movement information and/or structural characteristic information, a position of a region of interest (ROI) of the object to be scanned (i.e., the processing device 120 may position the object). For instance, the position of the ROI of the object may be a position of the object with a movement speed less than a speed threshold. The processing device 120 may determine, based on the position of the ROI of the object, the one or more scan parameters, such as the scan range, the scan thickness, the scan spacing. The processing device 120 may cause the imaging component to perform the scan on the object based on the one or more scan parameters for obtaining the target image data of the object. As another example, the ultrasonic signal may be acquired during the scan of the object and indicate a movement state of the object during the scan of the object. The processing device 120 may obtain the target image data of the object by triggering the imaging component to perform the scan according to the movement information. For instance, according to the movement information, the processing device 120 may trigger the imaging component to acquire image data of the object in specific time intervals during the scan of the object, and trigger the imaging component to not acquire image data of the object in remaining time intervals during the scan of the object, which can reduce an impact of the scan on the object. More descriptions regarding the determination of the one or more scan parameters may be found elsewhere in the present disclosure (e.g., FIG. 8 and relevant descriptions thereof).

In some embodiments, the processing device 120 may determine, based on the movement information, a parameter set including one or more image reconstruction parameters. The processing device 120 may obtain image data of the object by causing the imaging component to perform a scan on the object. The processing 120 may obtain the target image data of the object based on the image data of the object and the one or more image reconstruction parameters. The one or more image reconstruction parameters may include a reconstruction range (e.g., defined by, e.g., a length and width, a diameter, etc. of a reconstruction FOV), a reconstruction center, a reconstruction image thickness, a reconstruction angle range, or the like, or any combination thereof. For the scan data (i.e., the image data) acquired during the scan, a portion of the image data may be selected for reconstruction by setting or adjusting the reconstruction angle range. The reconstruction angle range corresponding to the scan may be equal to a scan angle range (including a plurality of acquisition angles) of the scan or a portion thereof. Taking the imaging of the heart as an example, the processing device 120 may obtain image data of the object during one or more cardiac cycles. The processing device 120 may determine, based on the movement information of the heart, a target movement phase of the heart for each of the one or more cardiac cycles. During the target phase, the motion of the heart may be with a small amplitude or intensity. The processing device 120 may determine an acquisition angle corresponding to the target phase as a target angle. For each of the one or more cardiac cycles, the processing device 120 may determine the reconstruction angle range centered at the target angle based on a preset angle range. The processing device 120 may select image data acquired under the reconstruction angle(s) from the image data of the object as the target image data.

In some embodiments, the processing device 120 may obtain initial image data of the object by causing the imaging component to perform a scan on the object. The processing device 120 may obtain the target image data of the object based on the image data of the object and the movement information. For example, the processing device 120 may cause the imaging component to acquire the initial image data continuously according to a retrospective gating technique. The processing device 120 may obtain the target image data from the initial image data based on the movement information (e.g., the cardiac motion data or the respiratory motion data). For example, the initial image data may correspond to one or more cardiac cycles. The processing device 120 may identify specific time interval(s) (e.g., diastole phase(s)) from the one or more cardiac cycles based on the cardiac motion data. The processing device 120 may determine specific image data of the initial image data that is acquired at the specific time interval(s) as the target image data. The object may undergo a movement with a relatively small amplitude or intensity at the specific time interval(s), thereby reducing motion artifact(s) in image reconstruction. As another example, the initial image data may correspond to one or more respiratory cycles (e.g., one or more expiration periods). The processing device 120 may identify specific time interval(s) (e.g., an inspiration phase or an expiration phase) from the one or more specific respiratory cycles based on the respiratory motion data. The processing device 120 may determine specific image data of the initial image data that is acquired at the specific time interval(s) as the target image data. As still another example, the processing device 120 may correct the initial image data based on the movement information. The processing device 120 may determine the corrected initial image data as the target image data.

In some embodiments, the processing device 120 may determine, during the scan of the object, the target image data based on the movement information of the position of the object. For example, during the scan of the object, the processing device 120 may determine whether the movement state of the position of the object satisfies a preset condition based on the movement information of the position of the object. In response determining that the movement state of the position of the object satisfies the preset condition (e.g., a movement state in which the object needs to be during the scan), the processing device 120 may determine scan data acquired during the scan as the target image data of the object. In response to determining that the movement state of the position of the object does not satisfy the present condition, the processing device 120 may rescan the object using the imaging component to obtain rescan image data. The processing device 120 may determine the rescan image data as the target image data of the object.

It should be noted that the description of the process 700 is provided for the purposes of illustration, and not intended to limit the scope of the present disclosure. For persons having ordinary skills in the art, various variations and modifications may be conducted under the teaching of the present disclosure. For example, operations 702 and 704 may be integrated into a single operation. As another example, an additional operation for image reconstruction based on the target image data may be added after operation 706. As still another example, the operation 706 may be replaced by an operation for generating a target image. In the operation, the processing device 120 may obtain image data of the object acquired during a scan of the object using the imaging component. The processing device 120 may reconstruct an initial image (or a tomography image sequence) based on the image data. The processing device 120 may generate the target image of the object by correcting, based on the movement information, the initial image (or the tomography image sequence). In further another example, the operation 706 may be omitted. An additional operation for analyzing image data of the object may be added. For instance, the processing device 120 may obtain image data of the object by causing the imaging component to perform a scan on the object. During the scan, the object may undergo different non-rigid motions. The processing device 120 may generate, based on the image data of the object, images of the object. The processing device 120 may analyze differences of the images of the object under the different non-rigid motions for research purposes. However, those variations and modifications may not depart from the protection of the present disclosure.

Figure 8:
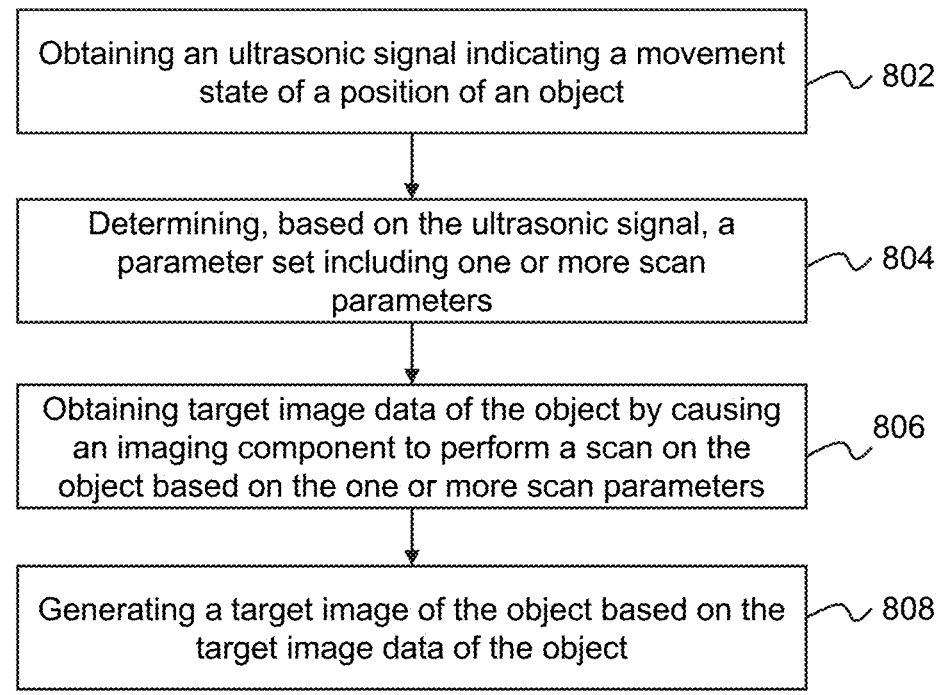
FIG. 8 is a flowchart illustrating an exemplary process for generating a target image of an object according to some embodiments of the present disclosure.

FIG. 8 is a flowchart illustrating an exemplary process for generating a target image of an object according to some embodiments of the present disclosure. Process 800 may be implemented in the medical system 100 illustrated in FIG. 1. For example, the process 800 may be stored in the storage device 130 and/or the storage device 220 in the form of instructions (e.g., an application), and invoked and/or executed by the processing device 120 (e.g., the processing device 120 illustrated in FIG. 1, or one or more modules in the processing device 120 illustrated in FIG. 6). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 802, the processing device 120 (e.g., the obtaining module 610) may obtain an ultrasonic signal indicating a movement state of a position of an object.

In some embodiments, the ultrasonic signal may be acquired by at least one laser ultrasonic component of a medical device (e.g., the at least one laser ultrasonic component 160 of the medical device 110, the laser ultrasonic component 420 of the medical device 400, or the laser ultrasonic component 520 of the medical device 500). For example, the ultrasonic signal may be acquired before a scan of the object using an imaging component of the medical device. As another example, the ultrasonic signal may be acquired during the scan of the object using the imaging component of the medical device. As still another example, laser sources of the at least one laser ultrasonic component may be arranged to be confocal at the position of the object to acquire the ultrasonic signal. More descriptions regarding the obtaining of the ultrasonic signal may be similar to that described in operation 702, which is not repeated herein.

In 804, the processing device 120 (e.g., the motion determination module 604, and/or the target image data determination module 606) may determine, based on the ultrasonic signal, a parameter set including one or more scan parameters.

In some embodiments, the processing device 120 may determine, based on the ultrasonic signal, movement information and/or structural characteristic information of the object as described in operation 704 in FIG. 7. Different movement information of the object may correspond to different scan parameters. The processing device 120 may determine the one or more scan parameters based on the movement information and/or the structural characteristic information of the object. For the PET scanner or the MRI scanner, the one or more scan parameters may include a scan range (e.g., including a scan center and a scanning diameter), a scan frequency (e.g., including gating information), a scan thickness (i.e., a thickness of a scan slice), a scan spacing (i.e., a distance of two scan slices), etc. During a scan of the object, the PET scanner (or the MRI scanner) may be caused to acquire image data of the object or stop acquiring image data of the object based on the scan frequency. For the CT scanner, the one or more scan parameters may include a scan time, a scan thickness, a scan spacing, a current time product, a scan range (e.g., including a scanning center and a scanning diameter), a tube voltage (e.g., a specific kilovolt (kV)) of a radiation source of the CT scanner, a scan angle, or the like, or any combination thereof. The current time product refers to a product of a tube current of the radiation source of the CT scanner and an exposure time during the scan. The scan time may correspond to time interval(s) during which the object undergoes a motion with a relatively small amplitude (e.g., time intervals when the object undergoes light organ peristalsis). For the MRI scanner, the one or more scan parameters may be arranged in a pulse sequence in time series. The pulse sequence may define scan parameters relating to one or more radiofrequency pulses, one or more phase encoding gradients according to which scan data (e.g., MR signals) of the object may be generated, times when one or more echo signals are acquired (i.e., echo times), etc.

In some embodiments, taking a CT scan as an example, the processing device 120 may determine, based on the ultrasonic signal acquired before the scan of the object, an ultrasonic image of the object. The ultrasonic image of the object may reflect the structural characteristic information of the object, and be used as a positioning image (i.e., a Topo image) of the object for the CT scan. The processing device 120 may determine the one or more scan parameters (e.g., the scan range, the scan thickness, the scan spacing, etc.) based on the ultrasonic image. Merely by way of example, the processing device 120 may identify an ROI to be scanned of the object in the ultrasonic image. The processing device 120 may determine the scan range based on the ROI to be scanned of the object. The scan range may include the ROI to be scanned of the object.

In some embodiments, the processing device 120 may determine the scan range based on the ROI identified in the ultrasonic image and the movement information of the object. For example, the ROI of the object may be subjected to a nonlinear deformation caused by the physiological motion of the object. The processing device 120 may determine the nonlinear deformation of the ROI based on the movement information of the object. The processing device 120 may determine, based on the ROI and the nonlinear deformation of the ROI, the scan range. The scan range may be larger than the ROI, such that when the ROI is subject to the nonlinear deformation caused by the physiological motion of the object, the ROI may be always within the scan range.

In some embodiments, the processing device 120 may determine the scan frequency based on the movement information of the object. For example, the processing device 120 may generate a motion curve based on the ultrasonic signal acquired before the scan of the object. The processing device 120 may determine the scan frequency based on the motion curve. The scan frequency may include predicted gating information reflecting when the imaging component acquires image data of the object and when the imaging component stops acquiring image data of the object. As another example, the processing device 120 may determine movement information of the object, such as motion speed, motion amplitude, motion intensity, etc. The processing device 120 may generate the gating signal for triggering the imaging component to acquire image data when the movement information satisfies a condition; the processing device 120 may generate the gating signal for causing the imaging component to not acquire image data when the movement information does not satisfy the condition. For instance, the processing device 120 may generate the gating signal for triggering the imaging component to acquire image data when the movement amplitude is less than a threshold amplitude, the movement intensity is less than a threshold intensity, or the movement speed is less than a threshold speed.

In some embodiments, the processing device 120 may determine the pulse sequence based on the movement information of the object. For example, the pulse sequence may be defined by one or more parameters relating to time, such as a repetition time (TR), an acquisition time (TA), an echo time (TE), etc. The processing device 120 may determine a gating signal based on the ultrasonic signal acquired before the scan of the object. The processing device 120 may determine, based on the gating signal, the one or more parameters relating to time. Merely by way of example, the processing device 120 may determine the acquisition time (TA) and/or the repetition time (TR) based on the gating signal. The processing device 120 may determine the pulse sequence based on the one or more parameters relating to time.

In 806, the processing device 120 (e.g., the target image data determination module 630 and the control module 640) may obtain target image data of the object by causing an imaging component to perform a scan on the object based on the one or more scan parameters.

In some embodiments, the processing device 120 may obtain the ultrasonic signal indicating a movement state of the position of the object during the scan of the object. The processing device 120 may determine a gating signal based on the ultrasonic signal acquired during the scan of the object. The processing device 120 may cause the imaging component to perform the scan based on the gating signal and the one or more scan parameters. According to the gating signal, the imaging component may be controlled whether to acquire image data of the object during the scan of the object in real-time. The processing device 120 may determine the image data acquired during the scan of the object as the target image data. Alternatively, the processing device 120 may cause the imaging component to perform the scan on the object based on the one or more scan parameters (e.g., the scan frequency). The processing device 120 may designate image data acquired during the scan of the object as the target image data. Taking an MRI scan as an example, the processing device 120 may obtain scan data of the object by causing the MRI scanner to perform a scan of the object according to a pulse sequence. The processing device 120 may determine, based on the movement information of the object, whether the motion state of the object satisfies a preset condition. In response to determining that the motion state satisfies the preset condition, the processing device 120 may directly use the scan data to fill one or more k-space lines corresponding to the pulse sequence in a k-space for obtaining the target image data (e.g., k-space data). In response to determining that the motion state does not satisfy the preset condition, the processing device 120 may correct the scan data and use the corrected scan data to fill the one or more k-space lines corresponding to the pulse sequence in the k-space for obtaining the target image data. Alternatively, the processing device 120 may remove the scan data and the one more k-space lines in the k-space corresponding to the pulse sequence may be not filled. In some embodiments, the processing device 120 may cause the MRI scanner to re-scan the object according to the pulse sequence to obtain second scan data and use the second scan data to fill the one or more k-space lines corresponding to the pulse sequence in the k-space for obtaining the target image data (e.g., k-space data) if the motion state of the object when the MRI scanner re-scans the object satisfies the preset condition. More descriptions regarding the obtaining of the target image data may be found elsewhere in the present disclosure (e.g., operation 706 in FIG. 7 and the description thereof).

In 808, the processing device 120 (e.g., the reconstruction module 650) may generate a target image of the object based on the target image data of the object.

In some embodiments, the target image may include a 2D image, a 3D image, or the like, or any combination thereof. For example, the target image may include a 3D image including a tomographic image sequence. In some embodiments, the processing device 120 may generate the target image of the object by reconstructing the target image data using one or more image reconstruction algorithms. For example, the one or more image reconstruction algorithms may include a 2D Fourier transform technique, a back projection technique (e.g., a convolution back projection technique, a filtered back projection technique), an iteration reconstruction technique, etc. Examples of iterative reconstruction techniques may include a simultaneous algebraic reconstruction technique (SART), a simultaneous iterative reconstruction technique (SIRT), an ordered subset convex technique (OSC), ordered subset maximum likelihood methodologies, an ordered subset expectation maximization (OSEM) methodology, an adaptive statistical iterative reconstruction technique (ASIR) methodology, a least squares QR methodology, an expectation maximization (EM) methodology, an OS-separable paraboloidal surrogates technique (OS-SPS), an algebraic reconstruction technique (ART), a Kacsmarz reconstruction technique, or any other iterative reconstruction technique or methodology that meets application-specific requirements.

In some embodiments, the processing device 120 may generate an initial image of the object based on the target image data. The processing device 120 may determine the target image of the object by correcting the initial image. For example, the processing device 120 may correct the initial image based on movement information of the object that is determined based on the ultrasonic signal.

It should be noted that the description of the process 800 is provided for the purposes of illustration, and not intended to limit the scope of the present disclosure. For persons having ordinary skills in the art, various variations and modifications may be conducted under the teaching of the present disclosure. For example, operation 804 may be divided into sub-operations, one of which is for determining the movement motion based on the ultrasonic signal, and another of which is for determining the one or more scan parameters based on the movement motion. As another example, an additional operation for causing the target image to be displayed may be added after operation 808. However, those variations and modifications may not depart from the protection of the present disclosure.

Figure 9:
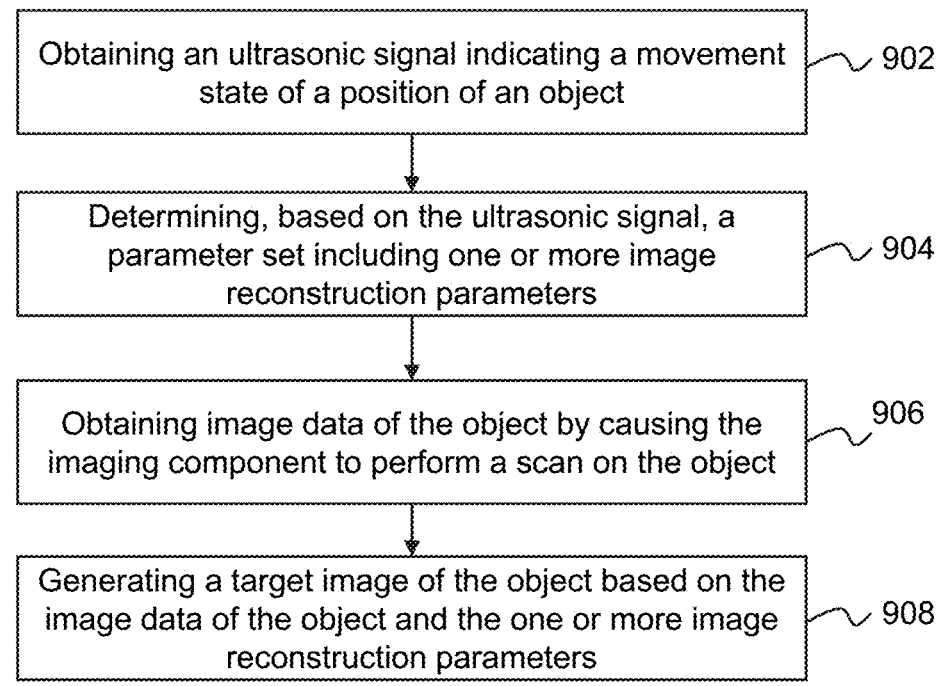
FIG. 9 is a flowchart illustrating an exemplary process for generating a target image of an object according to some embodiments of the present disclosure.

FIG. 9 is a flowchart illustrating an exemplary process for generating a target image of an object according to some embodiments of the present disclosure. Process 900 may be implemented in the medical system 100 illustrated in FIG. 1. For example, the process 900 may be stored in the storage device 130 and/or the storage device 220 in the form of instructions (e.g., an application), and invoked and/or executed by the processing device 120 (e.g., the processing device 120 illustrated in FIG. 1, or one or more modules in the processing device 120 illustrated in FIG. 6). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 902, the processing device 120 (e.g., the obtaining module 610) may obtain an ultrasonic signal indicating a movement state of a position of an object.

In some embodiments, the ultrasonic signal may be acquired during a scan of the object and indicate the movement state of the object during the scan of the object. More descriptions regarding the obtaining of the ultrasonic signal may be similar to that described in operations 702 and 802, which are not repeated herein.

In 904, the processing device 120 (e.g., the motion determination module 604, and/or the target image data determination module 606) may determine, based on the ultrasonic signal, a parameter set including one or more image reconstruction parameters.

In some embodiments, the processing device 120 may determine, based on the ultrasonic signal, movement information and/or structural characteristic information of the position of the object as described in operation 704 in FIG. 7. Different movement information of the object may correspond to different image reconstruction parameters. The processing device 120 may determine the one or more image reconstruction parameters based on the movement information and/or the structural characteristic information of the object. The one or more image reconstruction parameters may include a reconstruction range (e.g., defined by, e.g., a length and width, a diameter, etc. of a reconstruction FOV), a reconstruction center, a reconstruction image thickness, a reconstruction angle range, or the like, or any combination thereof. For example, the reconstruction angle range may correspond to time interval(s) when the object undergoes a motion with relatively small amplitude or intensity.

In 906, the processing device 120 (e.g., the target image data determination module 630 and the control module 640) may obtain image data of the object by causing an imaging component to perform the scan on the object.

In some embodiments, the processing device 120 may cause the imaging component to perform the scan on the object for acquiring the image data continuously, at the same time, the processing device 120 may obtain the ultrasonic signal. In other words, the ultrasonic signal and the image data of the object may be acquired synchronously. The processing device 120 may process the image data based on the ultrasonic signal. For example, the processing device 120 may determine movement information of the object based on the ultrasonic signal. The movement information of the object may indicate the movement state of the object changing over time. The processing device 120 may process the image data based on the movement state of the object changing over time according to a retrospective gating technique. For example, the processing device 120 may determine, based on the movement information of the object, a retrospective gating curve indicating whether image data acquired at a time (or period) is retained. As a further example, the retrospective gating curve may include corresponding to continuous time periods. Value 1 corresponding to a time period may indicate retaining image data that is acquired during the time period and value 0 may indicate not retaining image data acquired during the time period. The processing device 120 may determine a time period corresponding to value 1 in the retrospective gating curve if the movement state during the time period satisfies a condition or corresponding to value 0 if the movement state during the time period does not satisfy the condition.

More descriptions regarding the obtaining of the image data may be found elsewhere in the present disclosure (e.g., operation 706, operation 806, and the descriptions thereof).

In 908, the processing device 120 (e.g., the reconstruction module 650) may generate a target image of the object based on the image data of the object and the one or more image reconstruction parameters.

In some embodiments, the processing device 120 may determine target image data based on the image data of the object and the one or more image reconstruction parameters. The processing device 120 may generate the target image of the object based on the target image data and the one or more reconstruction parameters. Alternatively, the processing device 120 may directly generate the target image by reconstructing the image data of the object based on the one or more image reconstruction parameters. In some embodiments, the processing device 120 may generate the target image of the object based on the image data of the object and the one or more reconstruction parameters using one or more image reconstruction algorithms, more descriptions of which may be found elsewhere in the present disclosure (e.g., operation 808 in FIG. 8 and relevant descriptions thereof).

In some embodiments, during a four-dimensional image reconstruction (e.g., a PET reconstruction including time information), image data may need to be divided into a plurality of sub-image data according to a plurality of time intervals for reconstruction. Each sub-image data may be acquired during one of the plurality of time intervals. The plurality of time intervals may be continuous time intervals. Each of the plurality of time intervals may include a time length (e.g., 0.8 seconds, 0.5 seconds, 0.2 seconds, etc.). Time lengths of the plurality of time intervals may be the same or different. The processing device 120 may determine the time length of each of the time intervals based on the ultrasonic signal of the object. For example, the processing device 120 may determine the movement information of the object based on the ultrasonic signal. The movement information may indicate one or more motion cycles (e.g., cardiac cycles) during which the image data is acquired and information (e.g., a heart rate) in each of the one or more motion cycles. The plurality of time intervals may correspond to the one or more motion cycles. That is, the duration of each of the one or more motion cycles may be equal to the duration of one of the plurality of time intervals. The processing device 120 may determine a time length of a specific time interval of the plurality of time intervals based on a heart rate in a cardiac cycle that the specific time interval belongs to. Time intervals belong to cardiac cycles with different heart rates may correspond to different time lengths. The faster a heart rate of a cardiac cycle is, the less a time length of a time interval belongs to the cardiac cycle may be. For instance, the processing device 120 may determine the plurality of time intervals based on the one or more motion cycles during which the image data is acquired. The processing device 120 may divide the image data according to the plurality of time intervals. The processing device 120 may reconstruct the target image of the object based on the divided image data.

In some embodiments, the processing device 120 may generate an initial image of the object based on the image data and the one or more image reconstruction parameters. The processing device 120 may determine the target image of the object by correcting the initial image. For example, the processing device 120 may correct the initial image based on movement information of the object that is determined based on the ultrasonic signal.

It should be noted that the description of the process 900 is provided for the purposes of illustration, and not intended to limit the scope of the present disclosure. For persons having ordinary skills in the art, various variations and modifications may be conducted under the teaching of the present disclosure. For example, operation 904 may be divided into sub-operations, one of which is for determining the movement motion based on the ultrasonic signal, and another of which is for determining the one or more image reconstruction parameters based on the movement motion. As another example, an additional operation for causing the target image to be displayed may be added after operation 908. However, those variations and modifications may not depart from the protection of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by the present disclosure, and are within the spirit and scope of the exemplary embodiments of the present disclosure.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

What is claimed is:

1. A system, comprising:
   at least one storage device including a set of instructions; and
   at least one processor configured to communicate with the at least one storage device, wherein when executing the set of instructions, the at least one processor is configured to direct the system to perform operations including:
   obtaining an ultrasonic signal indicating a movement state of a position of an object, the ultrasonic signal being acquired by at least one laser ultrasonic component of a medical device;
   determining, based on the ultrasonic signal, movement information of the position of the object; and
   obtaining, based on the movement information of the position, target image data of the object using an imaging component of the medical device, wherein the at least one laser ultrasonic component includes a target laser ultrasonic component arranged along a reference axis that forms a tilting angle with a vertical line, the vertical line being a line perpendicular to a horizontal plane that is parallel to a ground, and the tilting angle being less than a preset angle.

2. The system of claim 1, wherein the ultrasonic signal is acquired during a scan of the object using the imaging component or before the scan of the object using the imaging component.

3. The system of claim 1, wherein the imaging component includes at least two detection rings, the target laser ultrasonic component being disposed between a pair of adjacent detection rings of the at least two detection rings.

4. The system of claim 1, wherein the medical device includes a holder configured to support the at least one laser ultrasonic component.

5. The system of claim 1, wherein each of the at least one laser ultrasonic component includes a first laser source and a second laser source.

6. The system of claim 5, wherein the first laser source is configured to emit an energy pulse to the object for generating the ultrasonic signal and the second laser source is configured to detect the ultrasonic signal.

7. The system of claim 1, wherein the obtaining, based on the movement information of the position, target image data of the object using an imaging component of the medical device includes:
   determining, based on the movement information, a parameter set including one or more scan parameters; and
   obtaining the target image data of the object by causing the imaging component to perform a scan on the object based on the one or more scan parameters.

8. The system of claim 1, wherein the obtaining, based on the movement information of the position, target image data of the object using an imaging component of the medical device includes:
   determining, based on the movement information, a parameter set including one or more image reconstruction parameters;
   obtaining image data of the object by causing the imaging component to perform a scan on the object; and
   obtaining the target image data of the object based on the image data of the object and the one or more image reconstruction parameters.

9. The system of claim 1, wherein the obtaining, based on the movement information of the position, target image data of the object using an imaging component of the medical device includes:
   obtaining the target image data of the object by triggering the imaging component to perform a scan according to the movement information.

10. The system of claim 1, wherein the obtaining, based on the movement information of the position, target image data of the object using an imaging component of the medical device includes:
    obtaining initial image data of the object by causing the imaging component to perform a scan on the object; and
    obtaining the target image data of the object based on the initial image data of the object and the movement information.

11. The system of claim 1, wherein the determining, based on the ultrasonic signal, movement information of the position of the object includes:
    generating, based on the ultrasonic signal, an ultrasonic image or a motion curve of the object; and
    determining, based on the ultrasonic image or the motion curve of the object, the movement information of the position of the object.

12. The system of claim 1, wherein the ultrasonic signal indicates the movement state of the position inside the object.

13. A system, comprising:
    a medical device including:
    at least one laser ultrasonic component configured to acquire an ultrasonic signal indicating a movement state of a position of an object; and
    an imaging component configured to acquire, based on the ultrasonic signal, image data of the object, wherein the at least one laser ultrasonic component includes a target laser ultrasonic component arranged along a reference axis that forms a tilting angle with a vertical line, the vertical line being a line perpendicular to a horizontal plane that is parallel to a ground, and the tilting angle being less than a preset angle.

14. The system of claim 13, wherein the ultrasonic signal indicates the movement state of the position inside the object.

15. The system of claim 13, wherein the imaging component includes at least two detection rings, the target laser ultrasonic component being disposed between a pair of adjacent detection rings of the at least two detection rings.

16. The system of claim 13, wherein the imaging device includes a holder configured to support the at least one laser ultrasonic component.

17. The system of claim 13, wherein each of the at least one laser ultrasonic component includes a first laser source and a second laser source.

18. The system of claim 17, wherein the first laser source is configured to emit an energy pulse to the object for generating the ultrasonic signal and the second laser source is configured to detect the ultrasonic signal.

19. The system of claim 1, wherein
the imaging component includes a first imaging subcomponent of a first imaging modality and a second imaging subcomponent of a second imaging modality,
the first imaging subcomponent includes a gantry with a bore, the bore includes a first end facing the second imaging subcomponent and a second end away from the second imaging subcomponent,
the target laser ultrasonic component locates at the first end or the second end.

20. The system of claim 13, wherein
the imaging component includes a first imaging subcomponent of a first imaging modality and a second imaging subcomponent of a second imaging modality,
the first imaging subcomponent includes a gantry with a bore, the bore includes a first end facing the second imaging subcomponent and a second end away from the second imaging subcomponent, the target laser ultrasonic component locates at the first end or the second end.

* * * * *